United States Patent [19]
Khan et al.

[11] Patent Number: 5,686,096
[45] Date of Patent: Nov. 11, 1997

[54] MEDICAL DEVICE FOR THE PROTECTION OF A CATHETER PENETRATION SITE

[75] Inventors: Mohammad A. Khan, Sandy; Minh Quang Hoang, Taylorsville; Gregory J. Mann, West Jordan, all of Utah

[73] Assignee: Becton Dickinson and Company, Franklin Lakes, N.J.

[21] Appl. No.: 577,359

[22] Filed: Dec. 22, 1995

[51] Int. Cl.$^6$ ............................. A61K 9/70; A61F 13/02; A61F 13/20; C08L 15/00

[52] U.S. Cl. ..................... 424/443; 424/447; 424/448; 424/449; 604/306; 604/332; 604/385.1; 523/111; 523/122

[58] Field of Search .................................. 424/443, 447, 424/448, 449; 604/306, 385.1, 332; 523/111, 122

[56] References Cited

U.S. PATENT DOCUMENTS

| | | | |
|---|---|---|---|
| Re. 31,887 | 5/1985 | Hodgson | 428/355 |
| 4,374,126 | 2/1983 | Cardarelli et al. | 424/81 |
| 4,397,641 | 8/1983 | Jacobs | 604/180 |
| 4,747,401 | 5/1988 | Potter et al. | 128/156 |
| 4,915,694 | 4/1990 | Yamamoto et al. | 604/180 |
| 5,092,323 | 3/1992 | Riedel et al. | 602/54 |
| 5,117,981 | 6/1992 | Crawford et al. | 206/570 |
| 5,175,977 | 1/1993 | Crawford et al. | 53/399 |
| 5,195,981 | 3/1993 | Johnson | 604/180 |
| 5,304,146 | 4/1994 | Johnson et al. | 604/180 |
| 5,352,456 | 10/1994 | Fallon et al. | 424/448 |
| 5,354,282 | 10/1994 | Bierman | 604/180 |
| 5,380,294 | 1/1995 | Persson | 604/180 |
| 5,382,239 | 1/1995 | Orr et al. | 604/177 |
| 5,536,263 | 7/1996 | Rolf et al. | 604/307 |

OTHER PUBLICATIONS

"Polyvinyl Ether Adhesives," Handbook of Adhesives, Reinhold Publishing Corp. 1962, pp. 400–408.

"Development of a Safe and Effective One–Minute Preoperative Skin Preparation," by Alexander, MD, et al., Arch Surg. – vol. 120, Dec. 1985, pp. 1357–1361.

"Evaluation of Dressing Regimens for Prevention of Infection With Peripheral Intravenous Catheters," JAMA, Nov. 6, 1987 – vol. 258, No. 17, pp. 2396–2403.

"Dow Corning® 355 Medical Adhesive," Medical Products Business, Dow Corning Corporation, Midland, Michigan 48640.

"Boyd Cellular Products," Boyd Corporation, 6630 Owens Drive, Pleasanton, CA 94588.

"Scott Polyurethane Foam For Reservoiring & Delivering," Scott Paper Company, Foam Division, 1500 East Second Street, Chester, PA 19013, pp. 1–4.

"Ultra Fine," Foam Fabrication • Sound Control, 707 Umatilla Street, Denver, CO 80204.

"Kevlar® Aramid Fiber – Technical Guide," DuPont Fibers, Kevlar Products, P.O. Box 80705, Laurel Run Building, Chestnut Run Plaza, Wilmington, DE 19880–0705, (Dec. 1992).

"Kevlar® Aramid – The Uncommon Material For Uncommon Solutions," E.I. duPont de Newmours & Co. (Inc.), Fibers Department, Kevlar Special Products, Chestnut Run Plaza, P.O. Box 80, 0705, Laurel Run Bldg.–2E, Wilmington, DE 19880–0705.

"Cosmocil® CQ – Polyhexamethylene Biguanide Hydrochloride Solution," ICI Americas Inc. Chemicals Division, Wilmington, DE 19897, Apr. 1986, pp. 1–6.

Primary Examiner—Thurman K. Page
Assistant Examiner—Kathryne E. Shelborne
Attorney, Agent, or Firm—Arthur D. Dawson; Eric M. Lee

[57] ABSTRACT

A medical device for protecting a catheter penetration site on the skin of a patient includes a resilient pad having a patient contacting side and at least one void therein for receiving and retaining a catheter at a catheter penetration site. The device has an adhesive on the patient contacting side of the pad for releasably adhering the pad to the patient's skin at the catheter penetration site and also includes a sufficient quantity of an antimicrobial agent to create a zone of microbial inhibition around the catheter penetration site.

24 Claims, 7 Drawing Sheets

MEDICAL DEVICE FOR THE PROTECTION OF A CATHETER PENETRATION SITE

FIELD OF INVENTION

This invention generally relates to percutaneous catheters and more particularly to protection of a catheter placement site into the skin of a patient.

BACKGROUND

Many medical procedures involve the use of percutaneous catheters inserted into the body of a patient for fluid infusion or removal. Often, the catheter remains in place for 24 to 48 hours. During this period, the catheter needs to be reliably positioned and accessible for attachment and detachment of fluid handling devices. In addition to the need to keep a catheter in position on the patient's skin, the placement site needs to be protected from microorganisms.

Many workers have developed devices to anchor or position the catheter and allow the needed access. Representative recently patented devices for catheter anchoring and positioning include: A Repositional Catheter Fixation Device (U.S. Pat. No. 5,382,239); Catheter Anchoring System (U.S. Pat. No. 5,354,282); and Windowed Vein Catheter Dressing (U.S. Pat. No. 5,380,294). These representative patents provide several different approaches to fixation of a percutaneous catheter onto a patient's skin. These patented devices address the need to locate the catheter and protect the site, but are somewhat complex and do not address the need to suppress growth of microorganisms at the catheter penetration site.

U.S. Pat. Nos. 5,117,981 and 5,175,977, commonly assigned with the present application, disclose aspects of a kit for preparing and dressing an intravenous catheter site. The kit disclosed in these referenced patents includes an antimicrobial agent useful for disinfecting the skin where the catheter is inserted.

Practitioners using percutaneous catheters do not rely just on devices such as those referenced above for fixation of catheters. It is a common practice to apply strips of adhesive tape across a catheter at a placement site to secure and protect the placement. Tape can strongly retain the catheter in position, but since most tapes are somewhat inelastic, movement of the skin or a fluid handling device can cause movement of the catheter in the blood vessel or at the penetration site. Additionally, when tape is used for this purpose, there are occasional occurrences of the catheter being dislodged or even cut during tape removal to access the catheter for attachment or detachment of fluid handling devices. Since, in many cases, the catheter remains in position for 24 to 48 or more hours, development of infections by common skin microorganisms at the penetration site are a concern, and practitioners also routinely inspect the penetration site for evidence of infection. Examination of the actual penetration site is sometimes difficult with the devices described above or when adhesive tape is used for securing the catheter. There is a need for a medical device that is compatible with most current practice techniques that would protect the catheter placement site. If the device allows easy access for attachment and detachment of fluid handling devices, allows the practitioner to examine the penetration site and suppresses growth of microorganisms around the penetration site, the practice of catheterization would be advanced. Additionally, if the catheter penetration site protection device additionally provided some protection against cutting the catheter during tape removal, a further benefit would be realized. Such a device is disclosed hereinbelow.

SUMMARY

A medical device of the present invention for protecting a catheter penetration site on the skin of a patient includes a resilient pad having a patient contacting side and at least one void therein to receive and to retain a catheter at the catheter penetration site. The pad has an adhesive on the patient contacting side for releasably adhering the pad to the patient's skin at the catheter penetration site. The device further includes a sufficient quantity of an antimicrobial agent to create a zone of microbial inhibition around the catheter penetration site.

The device of the present invention is simple to use. The invention fills a need not met by existing retention devices by including an antimicrobial agent releasable at the catheter penetration site that inhibits growth of microorganisms at the penetration site.

DETAILED DESCRIPTION

While this invention is satisfied by embodiments in many different forms, there are shown in the drawings and are herein described in detail preferred embodiments of the invention with the understanding that the present disclosure is to be considered exemplary of the principles of the invention and is not intended to limit the invention to the embodiments illustrated. The scope of the invention is measured by the appended claims and their equivalents.

Figure 1:
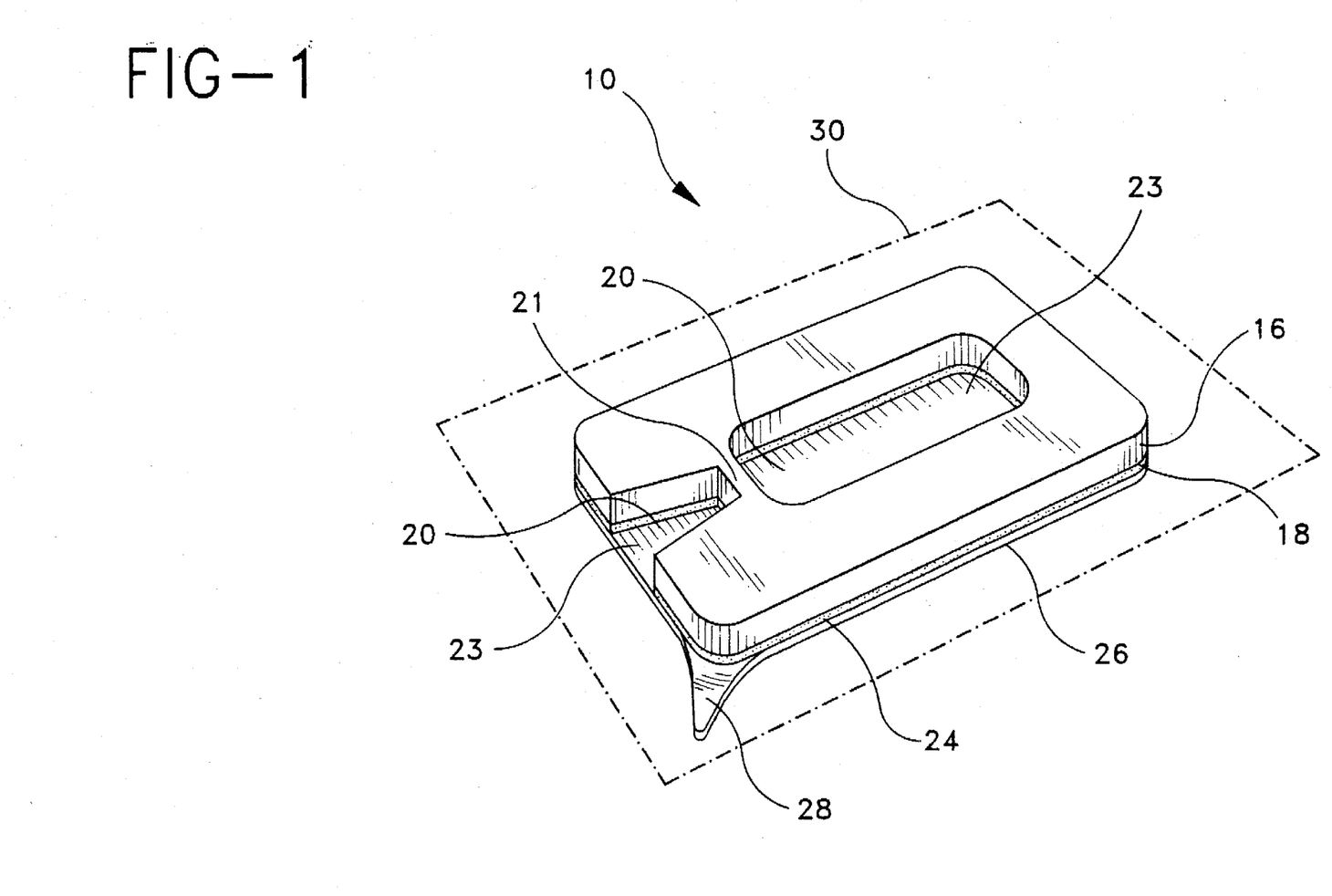
FIG. 1 is a perspective view of a preferred embodiment of a medical device of the present invention.
Figure 2:
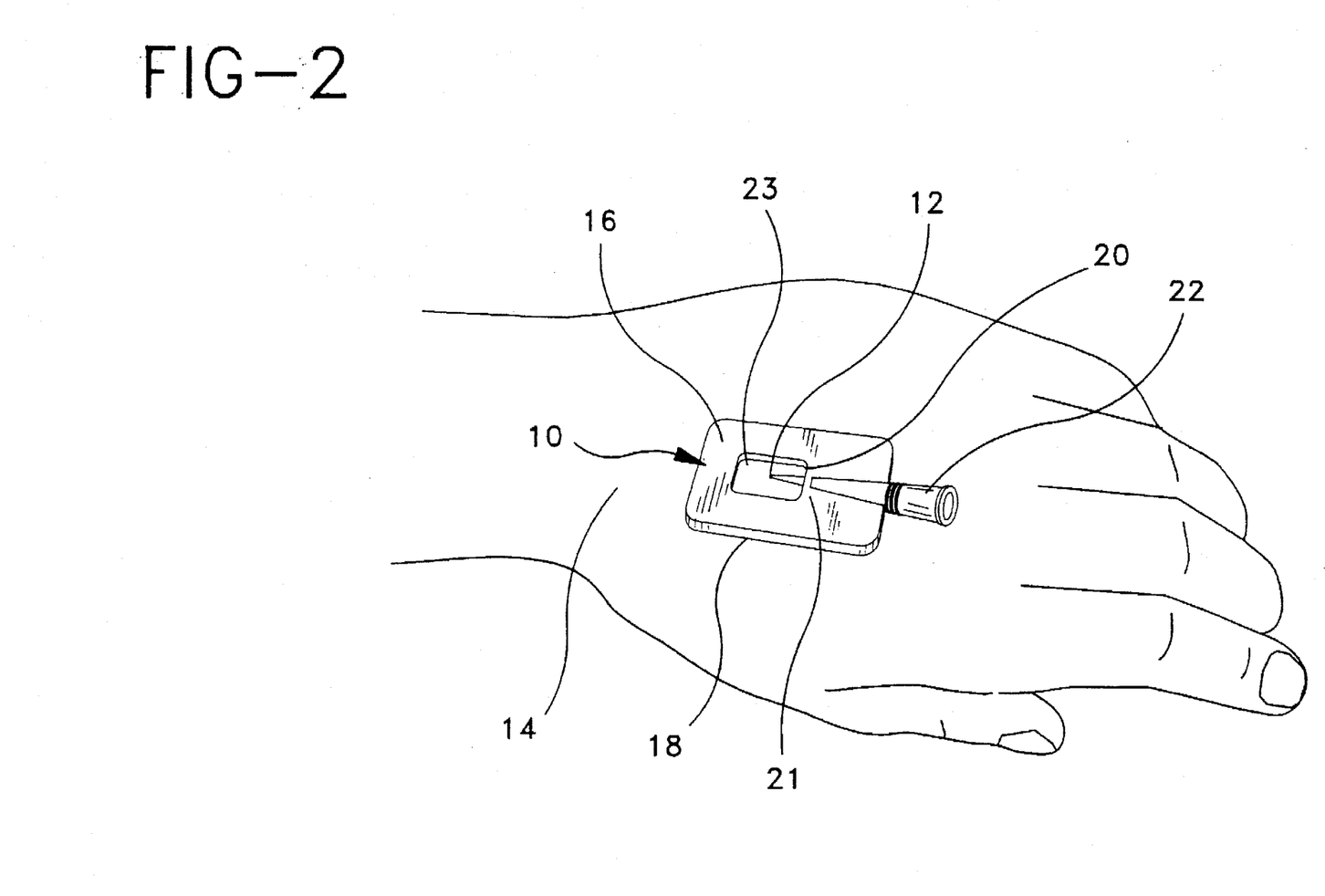
FIG. 2 is a perspective view of the device of FIG. 1 in use at a catheter placement site.
Figure 3:
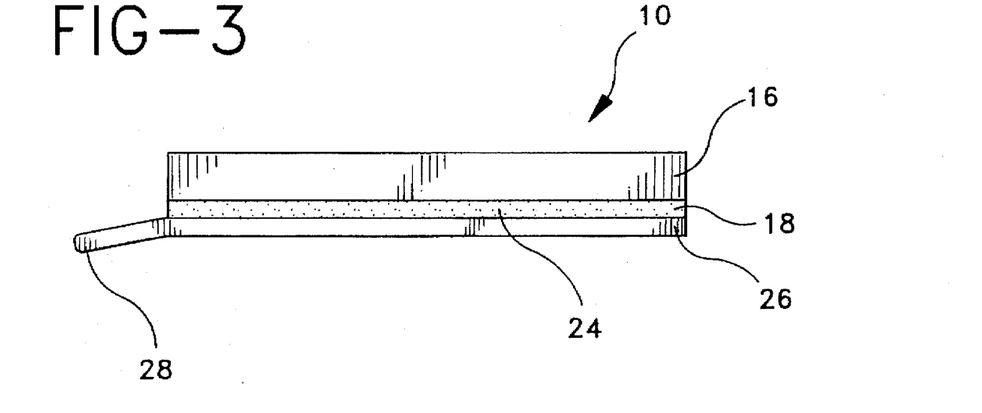
FIG. 3 is a side elevation of the device of FIG. 1.

Referring to FIGS. 1, 2 and 3, a preferred medical device 10 of the present invention for protecting a catheter penetration site 12 on a skin surface 14 of a patient includes a resilient pad 16 having a patient contacting side 18 and at least one void 20 to receive and to retain a catheter 22. Resilient pad 16 has an adhesive layer 24 applied to patient contacting side 18 for releasably adhering the pad to the patient's skin at catheter penetration site 12. Preferably, device 10 has a release cover 26, releasably attached to adhesive layer 24. Release cover 26 serves to protect the adhesive layer during assembly, shipping and storage of the device and preferably includes a tab 28 to facilitate removal of the release cover. Device 10 also includes a sufficient quantity of an antimicrobial agent to create a zone of inhibition of microbial growth on the patient's skin at and around the catheter penetration site when the device is positioned on the patient's skin.

As shown in FIGS. 1 and 2, void 20 may be divided into one or more openings 23 separated by a divider 21 that serves to restrain catheter 22. Preferably, void 20 is shaped so that when device 10 is positioned around catheter penetration site 12, the catheter is restrained and the penetration site is visible so that it can be readily inspected by the practitioner. Other shapes and configurations of resilient pad 16 and void 20 to accomodate particular catheters and applications are considered to be within the scope of the present invention. As schematically illustrated in phantom in FIG. 1, device 10 also is preferably sealed in a package 30 formed from materials substantially resistant to the passage of microorganisms and exposed to conditions rendering microorganisms non-viable.

Preferably, the antimicrobial agent is incorporated into adhesive layer 24, but a suitable zone of inhibition may also be created by incorporating the antimicrobial agent into resilient layer 16 or onto the surface of the adhesive. When the antimicrobial agent is incorporated into the adhesive, a concentration between about 0.1 percent to about 5.0 percent (wt./wt.) of the agent in the adhesive is suitable. Preferably, the concentration of the agent in the adhesive is between about 0.1 percent to about 1.0 percent. The concentration of antimicrobial agent used is dependent upon the particular agent selected and its availablility in the placement. Many antimicrobial agents are satisfactory for use in the present invention including, but not limited to, iodophors, chlorhexidine, salts of chlorhexidine, biguanides, salts of biguanides, phenolics, metallic ions, as well as antibiotic agents produced by microorganisms and their synthetic analogs and the like. Substantially the only restrictions on the selection and incorporation of the antimicrobial agent is the need for the antimicrobial agent to be available to form the zone of inhibition of microbial growth at and around the catheter penetration site and for compatibility between the antimicrobial agent, the resilient material and the adhesive selected.

FIGS. 4, 5, 6 and 7 illustrate alternatives to the medical device of the present invention for protecting a catheter penetration site. In these embodiments, the structure is substantially similar to the preferred device of FIGS. 1-3. Accordingly, substantially similar components that perform substantially similar functions are numbered identically to those of FIGS. 1-3 except that a suffix "A" is used in FIG. 4, and a suffix "B" is used in FIGS. 5-7.

Figure 4:
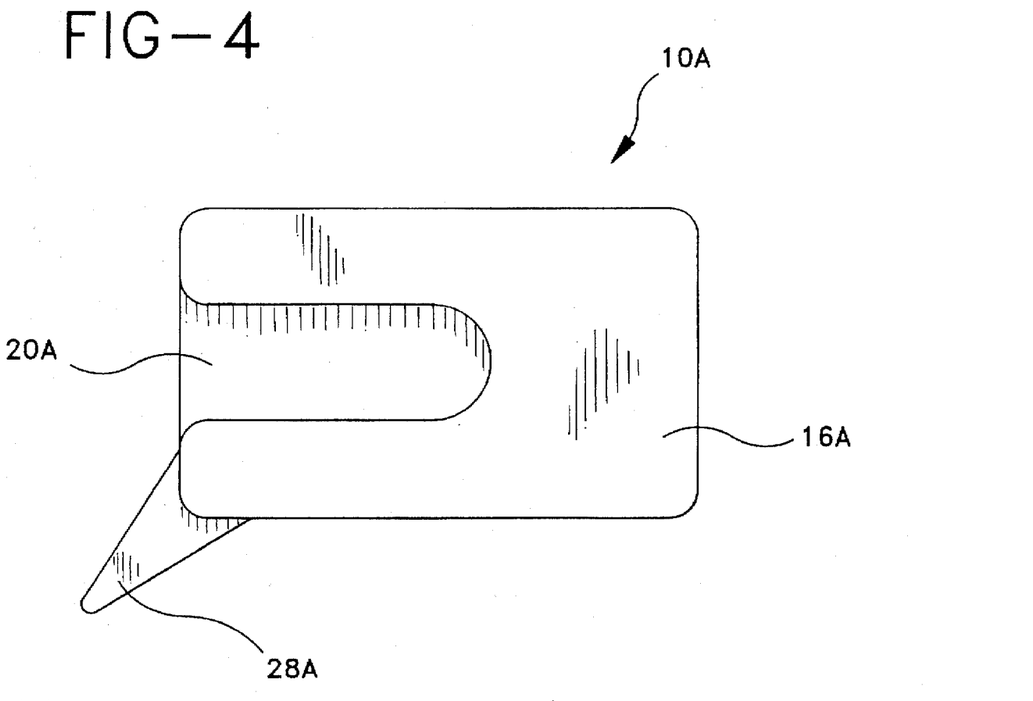
FIG. 4 is a top plan view of an alternate embodiment of the medical device of the present invention.

FIG. 4 illustrates device 10A where void 20A is a single opening shaped like a slot open at one end to allow positioning of the catheter within the slot and inspection of the catheter pentration site by the practitioner analogous to the usage illustrated in FIG. 2.

Figure 5:
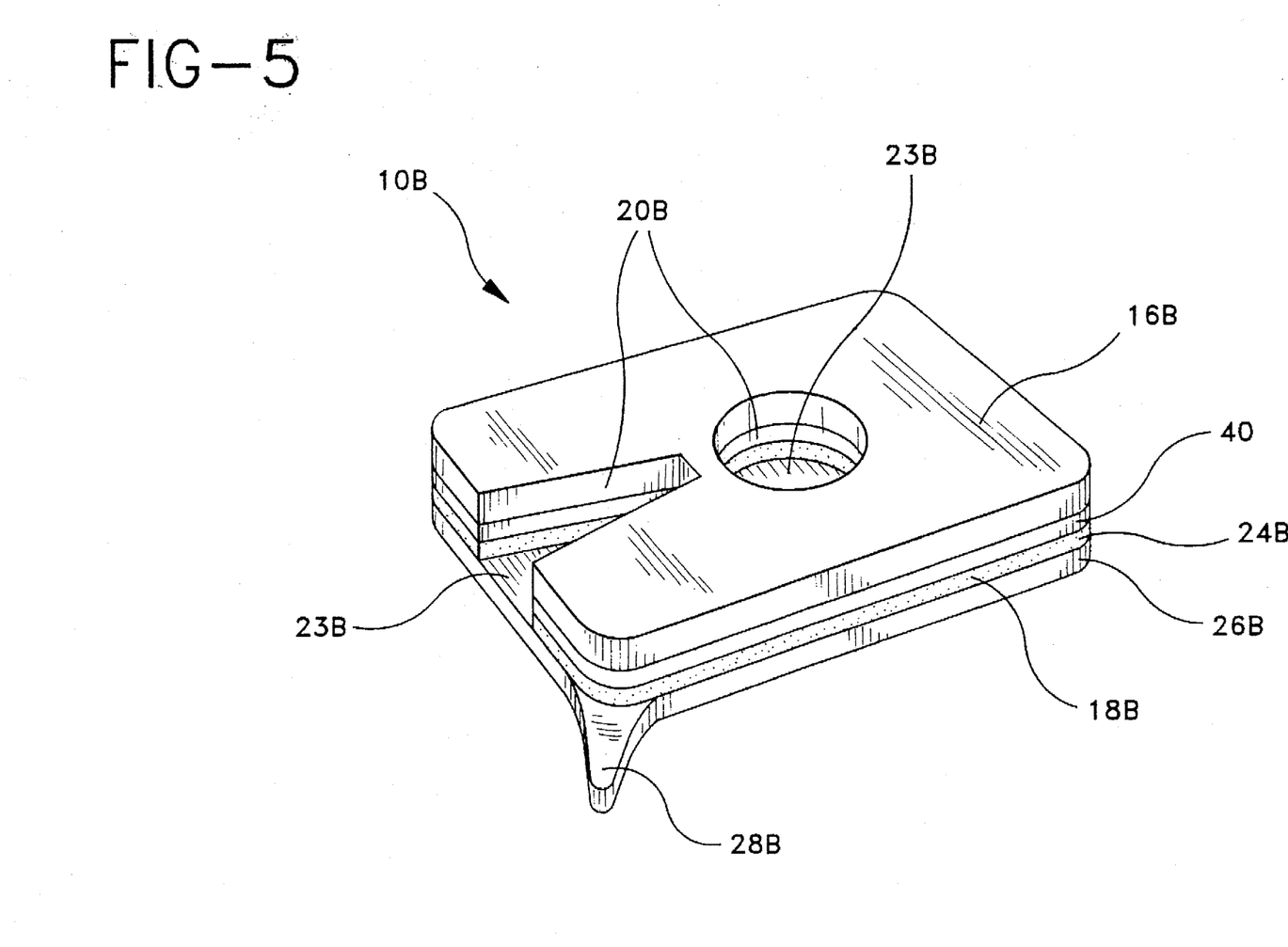
FIG. 5 is a perspective view of another embodiment of the medical device of the present invention.
Figure 6A:
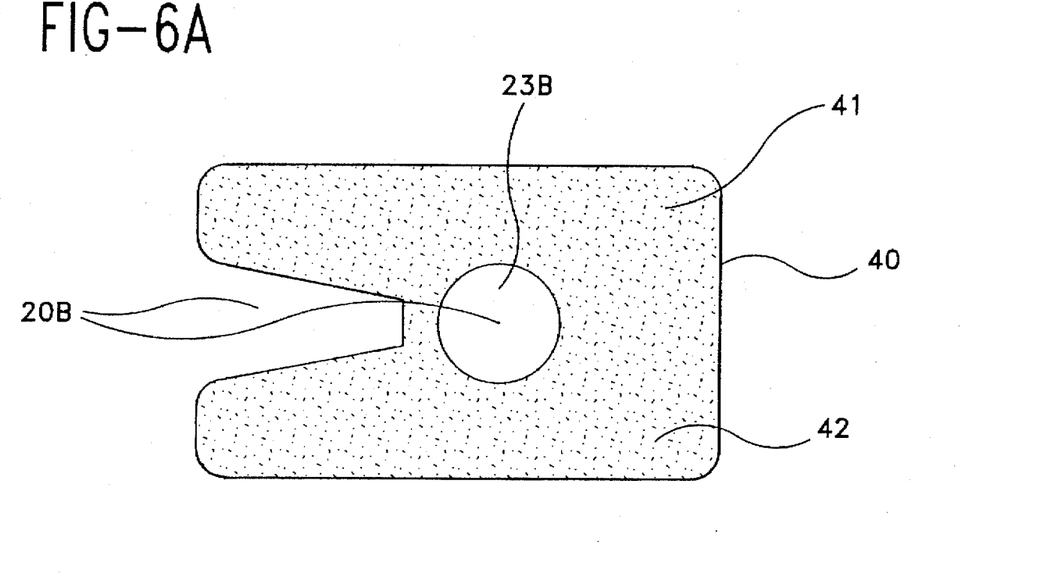
FIG. 6a is a schematic illustration of the cut resistant layer in the device of FIG. 5 formed from a non-woven material.
Figure 6B:
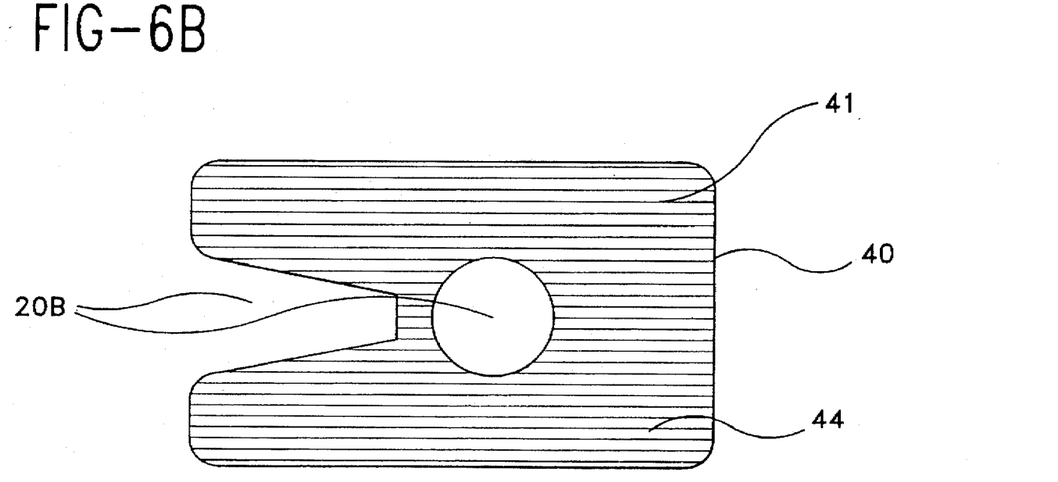
FIG. 6b is a schematic illustration of the cut-resistant layer in the device of FIG. 5 formed from filamentous material.
Figure 6C:
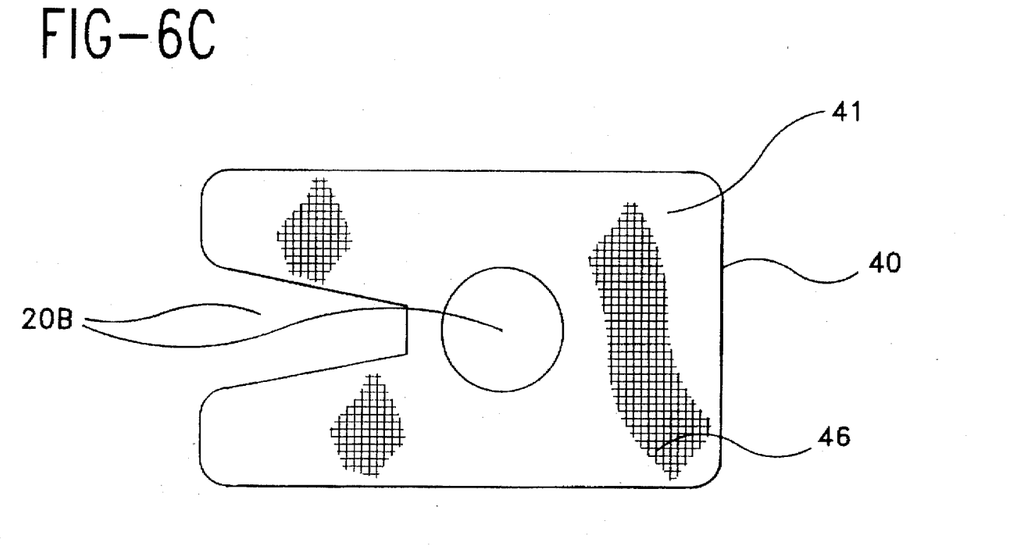
FIG. 6c is a schematic illustration of the cut-resistant layer in the device of FIG. 5 formed from a woven material.
Figure 7:
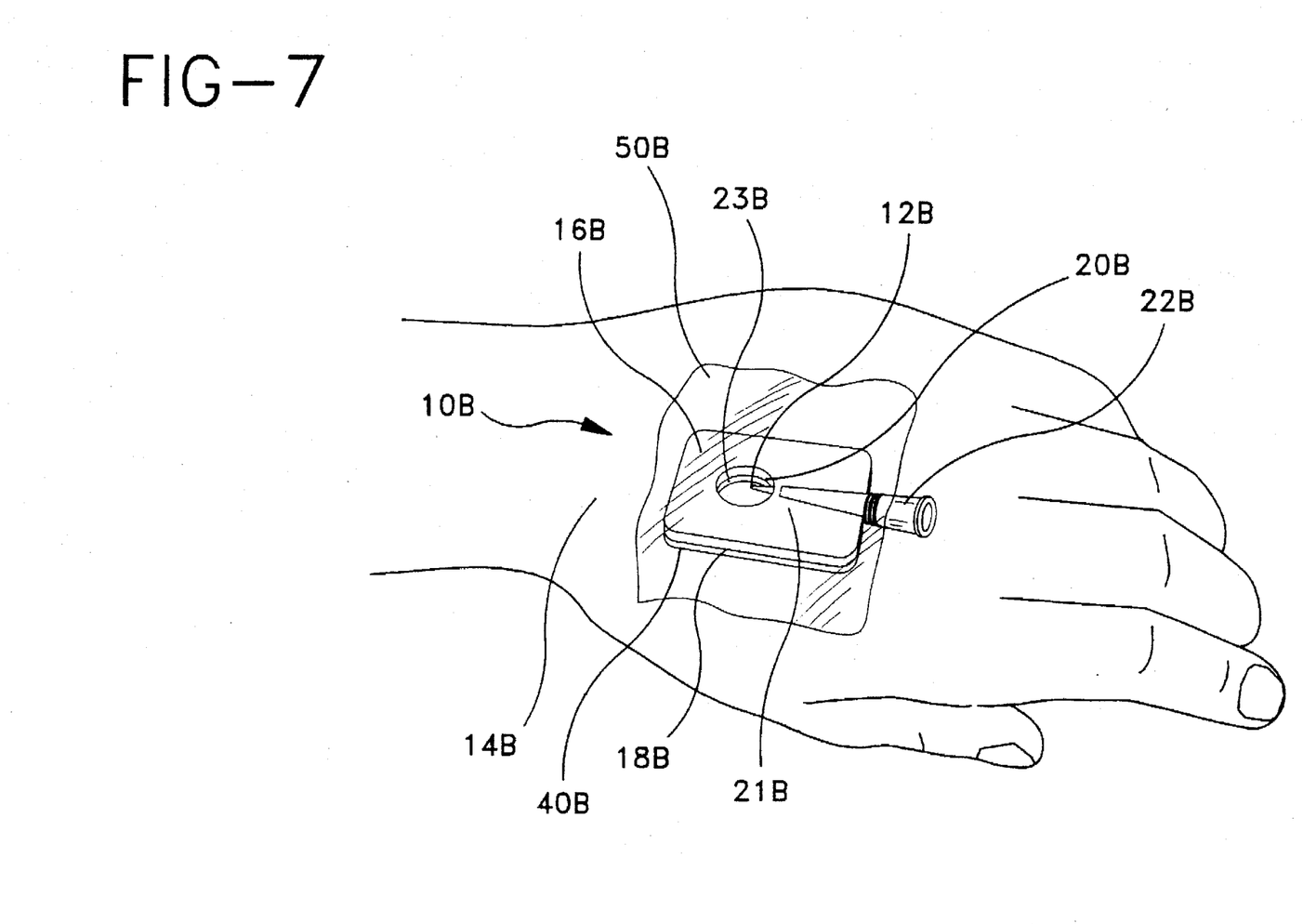
FIG. 7 is a perspective view of the device of FIG. 5 in use at a catheter placement site.

FIGS. 5-7 illustrate device 10B of the present invention including resilient foam layer 16B and a cut-resistant layer 40 with patient contacting side 18B. Adhesive layer 24B is applied to patient contacting side 18B to releasably adhere the device to a patient's skin. Cut-resistant layer 40 substantially provides protection to the catheter from inadvertent cutting with bandage scissors and the like when the practitioner is removing a tape cover, when tape is used to attach the catheter. Cut-resistant layer 40 may be formed from materials such as a non-woven material 42 as illustrated in FIG. 6a; filamentous material 44, as illustrated in FIG. 6b; and a woven material 46, as illustrated in FIG. 6c.

Figure 6D:
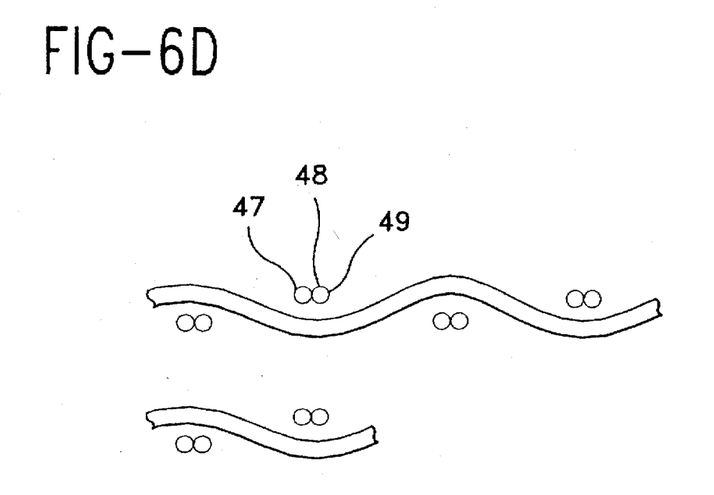
FIG. 6d is a schematic cross-section of the woven material from FIG. 6c formed from twisted strands.

Suitable fibers for forming cut-resistant layer 40 include, but are not limited to, polymeric materials such as polyamide and polyaramide. Kevlar™, a polyaramide material available from E. I. duPont, Wilmington, Del. is useful for forming cut-resistant layer 40. Metallic strands such as stainless steel and the like are also useful as fibers, filaments, woven and non-woven materials to form cut-resistant layer 40. Cut-resistant layer 40 may also be formed from combinations of metallic strands and polymeric fibers in woven, non-woven and filamentous structures. When metallic fibers, for woven material, non-woven material and as filaments are selected, two or more strands of stainless steel with a diameter greater than about 0.9 microns are preferably twisted together to form a single filament. Twisted metallic filaments formed from two or more strands have been shown to have greater resistance to cutting with scissors, commonly used in clinical situations to remove bandages, than an equivalent sized single strand filament. A schematic cross-section of woven layer 46 formed with filaments 48 formed from two twisted stainless steel strands 47 and 49 is schematically illustrated in FIG. 6d.

Cut-resistant layer 40 also may be formed from a continuous film or sheet of polymeric material between about 0.2 mm to about 2.0 mm thick. Suitable polymeric materials for this application include, but are not limited to, polypropylene, polyethylene, copolymers of polypropylene and polyethylene and the like. Polyethylene LDPE 9551 available from Dow, Midland, Mich. and polypropylene Profax PF091B available from Montell, Elkton, Md. may be formed into a sheet or film and bonded or laminated to foam layer 16B.

In FIG. 5, resilient foam layer 16B is shown forming the outermost layer of device 10B with cut-resistant layer 40 being intermediate adhesive layer 24B and resilient foam layer 16B. Alternative structures where cut-resistant layer 40 is outermost or incorporated into foam layer 16B are considered within the scope of the present invention, but not further illustrated in the interest of brevity.

FIG. 7 illustrates the placement of device 10B with a catheter 22B on the skin of a patient. In this illustration, device 10B with the catheter is covered with an adhesive tape 50 following a common practice for securing catheters. If the tape used is substantially transparent, the practitioner is able to inspect catheter penetration site 12B without removing the tape. However, many practitioners use cloth or paper tapes that are not substantially transparent. In this situation, when the practitioner removes the tape, scissors are often used. This tape removal may result in the catheter being cut by the scissors. Device 10B, with cut resistant layer 40, provides a resistance to the passage of the scissors and may alert the practitioner to the proximity of the scissors to the catheter and substantially reduce the possibility of damage to the catheter.

Suitable adhesives for adhering the catheter penetration device of the invention to a patient's skin include, but are not limited to, acrylic, acrylic copolymer and silicone pressure sensitive adhesives. Preferably, the pressure sensitive adhesive is not water soluble. A suitable acrylic pressure sensitive adhesive is I-780, available from Avery Medical Products, Painesville, Ohio. A suitable silicone pressure sensitive adhesive is 355 Medical Grade Adhesive, available from Dow-Corning, Midland, Mich. Preferably, the adhesive selected is substantially water insoluble. In the preferred embodiment, where the antimicrobial agent is incorporated into the adhesive, the antimicrobial agent may be mixed into the adhesive at between about 0.05 parts to about 5.0 parts per one hundred parts of adhesive. The adhesive then preferably is applied to the patient contacting side in a layer between about 0.1 mm to about 0.3 mm thick. Alternatives to mixing the antimicrobial agent into the adhesive include spraying or dipping the antimicrobial agent onto an adhesive film or tape and applying the film or tape to the patient adhering side of the device. Preferably, release cover 26 is placed over the adhesive layer to protect the adhesive during packaging, shipping and handling. Suitable release covers may be formed from coated papers or polymer films. Silicone treated papers are widely used as release covers. The particular material selected as a release cover is dependent upon the adhesive selected. The release cover is preferably easily peelable from the adhesive selected.

Suitable materials for forming resilient layer 16 include, but are not limited to, polymeric materials such as polyurethane foams and felts, polyethylene foam, polyimide foam, cellulose foam, silastic foam and vinyl nitrile foam. Representative sources for polyurethane foams and felts include, but are not limited to, Scott Paper Company, Foam Division, Chester, Pa. and Rogers Corp., East Woodstock, Conn. Suitable polyethylene foam is available from Voltek, Lawrence, Mass. Suitable polyimide foam is available from Imi-Tech, Elk Grove Village, Ill. Suitable vinyl nitrile foam is available from Ensolite, Mishwaka, Ind. Generally, resilient polymeric foams having a porosity between about 4 and 60 pores per cm and preferably between about 15 to about 40 pores per cm are satisfactory for forming the resilient layer in the present invention. Additionally, a foam with a density between about 0.2 to about 0.4 grams per cubic centimeter has been found to work well to form the resilient layer. Suitable resilient layer thickness is between about 2.5 mm to about 8.0 mm. The resilient layer preferably is between about 3 mm to about 6 mm thick.

Several examples of materials for device 10 were prepared with antimicrobial agent applied variously in the adhesive, adhesive applied to a film for application to the resilient foam and to the resilient foam itself. Samples of these several materials were tested for the ability to form a zone of microbial inhibition under and around a sample of the material placed in growth medium seeded with common microorganisms. For each example, an approximately one centimeter disc of the material to be tested was placed on Petri dishes coated with a suitable growth medium for the organism being tested. The dishes were seeded with the test microorganism and incubated at 37° C. The dishes were examined at 24 hours, 48 hours and 72 hours and the area where growth of the microorganisms was inhibited was measured. The results shown in Table 1 are reported as mm beyond the test sample disc circumference. In all cases tested, the growth of the test microorganisms was inhibited under the test sample disc.

Example 1

Tegaderm™ film (polyurethane film with pressure sensitive adhesive, available from 3M, St. Paul, Minn.) dipped in 4 percent (wt./wt.) aqueous chlorhexidine gluconate and dried.

Example 2

Woven cloth medical adhesive tape (Durapore™ medical adhesive tape available from 3M, St. Paul, Minn.) dipped in 4 percent (wt./wt.) aqueous chlorhexidine gluconate and dried.

Example 3

Silicone pressure sensitive adhesive mixed with 0.1 percent (wt./wt.) chlorhexidine diacetate and applied to polyurethane foam. (#355 medical grade adhesive, Dow-Corning, Midland, Mich., applied to Scott SIF polyurethane foam, Scott Paper Co., Foam Division, Chester, Pa.)

Example 4

Polyurethane foam (Scott SIF, Scott Paper Co., Foam Division, Chester, Pa.) dipped in 1 percent (wt./wt.) aqueous chlorhexidine diacetate and dried.

Example 5

Acrylic pressure sensitive adhesive mixed with 0.1 percent (wt./wt.) chlorhexidine diacetate and applied to polyurethane foam. (acrylic adhesive I-780, Avery Medical Products, Painesville, Ohio, Acquell® Foam, Denver, Colo.).

TABLE 1

| Microorganism | Example # | | | | |
| --- | --- | --- | --- | --- | --- |
| | 1 | 2 | 3 | 4 | 5 |
| s. Aureus | 2 mm | 5 mm | 0 mm | 1 mm | 2 mm |
| p. Aeruginosa | 1 mm | 2 mm | 0 mm | 1 mm | 1 mm |
| c. Albicans | 1 mm | 3 mm | 0.5 mm | 0 mm | 0 mm |
| e. Coli | 1 mm | 3 mm | 0 mm | 0.5 mm | 0 mm |

Zone of inhibition measurements made at 24, 48 and 72 hours were not materially different from each other, thus only one value is shown. The results show that the antimicrobial agents in the test examples are releasable from the samples and available to inhibit growth of microorganism at least under and in many instances beyond the test disc.

The medical device of the invention is simple to manufacture and to use. It provides a practitioner with a protector for a catheter placement that not only holds the catheter in position at the penetration site, but also inhibits microbial growth around the penetration site. The device also allows easy inspection of the penetration site by the practitioner and in some embodiments, substantially protects the catheter from inadvertent damage by scissors and the like during tape removal.

What is claimed is:

1. A medical device for protecting a catheter penetration site on the skin of a patient comprising:
   a resilient pad having a patient contacting side and at least one void therein to receive and to retain a catheter at a catheter penetration site wherein the resilient pad incorporates a cut resistant mechanism including aromatic polyamide fibers therein or a plurality of metallic strands twisted together to form a single filament therein;
   an adhesive on said patient contacting side of said pad for releasably adhering the pad to the patient's skin at the catheter penetration site; and
   a sufficient quantity of an antimicrobial agent to create a zone of microbial inhibition around the catheter penetration site.

2. The device of claim 1 wherein said resilient pad is formed from a polymeric material.

3. The device of claim 2 wherein said polymeric material is selected from the group consisting of polyurethane foams and felts, polyimide foam, polyethylene foam, silastic foam, vinyl nitrile foam, and cellulose foam.

4. The device of claim 1 wherein said adhesive is a pressure sensitive adhesive.

5. The device of claim 4 wherein said adhesive further comprises said antimicrobial agent, said agent being releasable from said adhesive when said pad is positioned on the patient's skin.

6. The device of claim 1 wherein said antimicrobial agent is selected from the group consisting of iodophors, chlorhexidine, salts of chlorhexidine, biguanides, salts of biguanides and phenolics.

7. The device of claim 1 wherein said antimicrobial agent is impregnated into said resilient pad, said agent being releasable from said pad when said pad is positioned on the patient's skin.

8. The device of claim 1 further comprising a release cover releasably adherent to said adhesive.

9. The device of claim 8 being sealed in a package formed from materials substantially resistant to the passage of microorganisms and having been exposed to conditions rendering any microorganisms therein non-viable.

10. The device of claim 1 wherein said resilient pad is between about 2.5 mm to about 8 mm thick.

11. The device of claim 1 wherein said at least one void comprises an opening through said pad having a shape to accommodate a hub of the catheter and provide visual access to the penetration site of the catheter.

12. The device of claim 11 wherein said at least one void further comprises an opening through the pad sized to accommodate said hub and another opening through the pad positioned to allow visual access to the catheter penetration site.

13. A medical device for protecting a catheter penetration site on the skin of a patient comprising:

a resilient polymeric foam pad having a patient contacting side and a void therein for receiving a catheter at a catheter penetration site wherein the resilient polymeric foam pad incorporates a cut resistant mechanism including aromatic polyamide fibers therein or a plurality of metallic strands twisted together to form a single filament therein;

an adhesive on said patient contacting side of said foam pad for releasably adhering said pad to the patient's skin;

a sufficient quantity of an antimicrobial agent selected from the group consisting of iodine, chlorhexidine, salts of chlorhexidine, biguanides, salts of biguanides, phenolics and antibiotics being mixed with said adhesive so that when said pad is releasably adherent to said patient's skin a zone of microbial inhibition is developed around said catheter penetration site by a release of said agent from said adhesive.

14. The medical device of claim 13 wherein said foam pad is formed from polyurethane.

15. The medical device of claim 13 wherein said adhesive is a silicone adhesive including between about 0.05 percent to about 5.0 percent (weight/weight) chlorhexidine diacetate.

16. The medical device of claim 13 further comprising a removable release sheet applied to said adhesive layer.

17. The medical device of claim 16 being sealed in a package formed from materials substantially resistant to the transmission of microorganisms and having been exposed to an environment rendering any microorganisms therein substantially nonviable.

18. A medical device for protecting a catheter penetration site on the skin of a patient comprising:

a resilient pad having a patient contacting side and an open ended slot therein to accommodate a catheter hub therein and to provide visual access to the catheter penetration site;

an adhesive on the patient contacting side of the resilient pad for releasably adhering the resilient pad to the patient's skin at the catheter penetration site; and an antimicrobial agent.

19. The medical device of claim 18 wherein the open ended slot includes a divider to divide the open ended slot into two separate openings.

20. The medical device of claim 18 wherein the antimicrobial agent is incorporated in the adhesive.

21. The medical device of claim 18 wherein the antimicrobial agent is incorporated into the resilient pad.

22. The medical device of claim 18 further including a cut resistant mechanism incorporated in the resilient pad.

23. The medical device of claim 22 wherein the cut resistant mechanism is aromatic polyamide fibers.

24. The medical device of claim 23 wherein the cut resistant mechanism is a plurality of metallic strands twisted together to form a single filament.

* * * * *